United States Patent
Yonaha et al.

(10) Patent No.: US 10,565,545 B2
(45) Date of Patent: Feb. 18, 2020

(54) DRUG INSPECTION SUPPORT APPARATUS AND METHOD

(71) Applicant: FUJIFILM TOYAMA CHEMICAL CO., LTD., Tokyo (JP)

(72) Inventors: Makoto Yonaha, Ashigarakami-gun (JP); Tetsuya Takamori, Ashigarakami-gun (JP); Ippei Takahashi, Ashigarakami-gun (JP); Seigo Sugimoto, Ashigarakami-gun (JP)

(73) Assignee: FUJIFILM TOYAMA CHEMICAL CO., LTD., Tokyo (JP)

( * ) Notice: Subject to any disclaimer, the term of this patent is extended or adjusted under 35 U.S.C. 154(b) by 649 days.

(21) Appl. No.: 14/633,505

(22) Filed: Feb. 27, 2015

(65) Prior Publication Data

US 2015/0178674 A1 Jun. 25, 2015

Related U.S. Application Data

(63) Continuation of application No. PCT/JP2013/073961, filed on Sep. 5, 2013.

(30) Foreign Application Priority Data

Sep. 27, 2012 (JP) ................................. 2012-213634

(51) Int. Cl.
*G06K 9/20* (2006.01)
*G06Q 10/08* (2012.01)
(Continued)

(52) U.S. Cl.
CPC ............. *G06Q 10/087* (2013.01); *G06K 9/20* (2013.01); *G06Q 50/22* (2013.01); *G16H 20/10* (2018.01)

(58) Field of Classification Search
CPC ........ G16H 20/13; G16H 10/60; G16H 50/20; A61J 3/00; A61J 1/10; A61J 2200/70; A61J 2205/10; A61J 2205/20; A61J 7/0084

See application file for complete search history.

(56) References Cited

U.S. PATENT DOCUMENTS 5,839,836 A * 11/1998 Yuyama ............. H04N 1/00127
 400/62
6,535,637 B1 * 3/2003 Wootton ................. B65B 57/00
 382/190

(Continued)

FOREIGN PATENT DOCUMENTS

JP 10-162116 A 6/1998
JP 2004-202140 A 7/2004
(Continued)

OTHER PUBLICATIONS

Extended European Search Report for European Application No. 13842029.4, dated Apr. 5, 2016.

(Continued)

*Primary Examiner* — Rachel L. Porter
(74) *Attorney, Agent, or Firm* — Birch, Stewart, Kolasch & Birch, LLP

(57) ABSTRACT

A drug inspection support apparatus inspects drugs that are prepared based on prescription information and are packaged in a prescription bag. A drug database stores drug master images of drugs that can be prepared. A first drug determination section compares drug master images from the drug database with a captured image obtained by capturing an image of prepared drugs, and determines drugs present in the captured image and the number of drugs. A list creation section creates a list displaying drug master images of drugs, which are prepared according to a prescription, and (Continued)

drug area images, which are determined to be respective drugs in a captured image, so that the positions thereof are aligned with one another.

20 Claims, 10 Drawing Sheets

(51) Int. Cl.
*G06Q 50/22* (2018.01)
*G16H 20/10* (2018.01)

(56) References Cited

U.S. PATENT DOCUMENTS

| | | | | |
|---|---|---|---|---|
| 2001/0041968 | A1* | 11/2001 | Hamilton | A61J 7/02 |
| | | | | 702/128 |
| 2002/0053183 | A1* | 5/2002 | Yuyama | A61J 7/04 |
| | | | | 53/131.2 |
| 2007/0000805 | A1 | 1/2007 | Van Den Brink | |
| 2009/0030722 | A1* | 1/2009 | Wiener | G06Q 50/22 |
| | | | | 705/2 |
| 2009/0294467 | A1 | 12/2009 | Yuyama et al. | |
| 2012/0200596 | A1* | 8/2012 | Gotou | B07C 5/38 |
| | | | | 345/625 |

FOREIGN PATENT DOCUMENTS

| | | | |
|---|---|---|---|
| WO | WO 2007/023829 A1 | 1/1971 | |
| WO | WO 02/25568 A2 | 3/2002 | |
| WO | WO-2011112606 A1 * | 9/2011 | ............... A61J 7/04 |
| WO | WO 2012/005004 A1 | 1/2012 | |
| WO | WO-2012056317 A2 * | 5/2012 | ............ A61J 7/0084 |

OTHER PUBLICATIONS

International Search Report, issued in PCT/JP2013/073961, dated Oct. 29, 2013. W
Written Opinion of the International Searching Authority, issued in PCT/JP2013/073961, dated Oct. 29, 2013.
Japanese Office Action, dated Aug. 25, 2015, for Japanese Application No. 2012-213634, with an English translation.
Chinese Office Action and Search Report issued in Chinese Application No, 201380044637.4 dated Aug. 3, 2017, together with an English translation of the Chinese Office Action.
Chinese Office Action, dated May 29, 2018, for corresponding Chinese Application No. 201380044637.4, along with an English translation.
Chinese Office Action and Search Report for Chinese Application No. 201380044637.4, dated Jan. 22, 2019, with partial English translation.
Chinese Office Action for Chinese Application No. 201380044637.4, dated Jun. 26, 2019, with an English translation.
European Office Action, dated Oct. 1, 2019, for European Application No. 13842029.4.

* cited by examiner

FIG. 2

DRUG DB

| ID | DRUG NAME | DRUG MASTER IMAGE | SIMILAR DRUG LIST |
|----|-----------|-------------------|-------------------|
| 001 | DRUG A | (IMAGE) | DRUGS X, Y |
| 002 | DRUG B | (IMAGE) | DRUGS X, Z |
| 003 | DRUG C | (IMAGE) | NONE |
| 004 | . . . | | |

FIG. 3

PRESCRIBED DRUGS    DRUGS TO BE COMPARED

| DRUGS A, B, C | | DRUGS A, B, C, X, Y, Z |

| PACKAGE NO. | DRUG 1 | DRUG 2 | DRUG 3 | DRUG 4 | DRUG 5 |
|---|---|---|---|---|---|
| MASTER DATA |  |  |  | . . . | . . . |
| 1 (FIRST DAY, MORNING) |  |  |  |  |  |
| 2 (FIRST DAY, DAYTIME) |  |  |  | | |
| 3 (FIRST DAY, EVENING) | | | | | |
| 4 (SECOND DAY, MORNING) | | | | | |
| . . . | | | | | |
| 30 (FIRST DAY, EVENING) | | | | | |

DRUG INSPECTION SUPPORT APPARATUS AND METHOD

CROSS-REFERENCE TO RELATED APPLICATIONS

This application is a Continuation of PCT International Application No. PCT/JP2013/073961 filed on Sep. 5, 2013, which claims priority under 35 U.S.C § 119(a) to Japanese Patent Application No. 2012-213634 filed on Sep. 27, 2012. Each of the above applications is hereby expressly incorporated by reference, in its entirety, into the present application.

BACKGROUND OF THE INVENTION

1. Field of the Invention

The present invention relates to a drug inspection support apparatus and method, and more particularly, to a drug inspection support apparatus and method for supporting inspection whether or not drugs dispensed according to a prescription are the same as the prescription.

2. Description of the Related Art

In recent years, separation of drug dispensing from the medical practice has been in progress. Accordingly, it is common for a patient to have a checkup in a medical institution and then bring a prescription written by the doctor to a pharmacy so that drugs can be prepared according thereto. In preparation, a plurality of drugs may be packaged in a container (hereinafter, also referred to as a prescription bag), such as a drug bag. During packaging, a plurality of drugs that should be taken at each specified dosage time, for example, at each specified dosage time in the morning, daytime, and evening, are packaged in one prescription bag.

In the packaging of drugs, for patient safety, a pharmacist inspects whether or not packaged drugs have been prepared according to the contents of a prescription written by a doctor. As a device for supporting the inspection of the pharmacist, for example, there is a device disclosed in JP1998-162116A (JP-H10-162116A). In JP1998-162116A (JP-H10-162116A), when sequentially transporting drugs packaged in prescription bags according to the prescription, the drugs in the prescription bags being transported are sequentially captured and the captured image of drugs in the prescription bags are displayed. In addition, image data of drugs to be prescribed is read from an image database and is displayed.

In JP1998-162116A (JP-H10-162116A), an image of each drug in the prescription bag being transported and an image read from the database are displayed at the same time for at least a predetermined period of time. In JP1998-162116A (JP-H10-162116A), an image obtained by actually capturing drugs transported on the conveyor belt and a graphic image of drugs to be contained in a prescription bag after being prescribed are displayed simultaneously for a predetermined time. Accordingly, a pharmacist inspects whether or not drugs are contained in prescription bags as prescribed by comparing both images.

SUMMARY OF THE INVENTION

In JP1998-162116A (JP-H10-162116A), the captured image and the master image from the database are simply displayed at the same time. By comparing both images, it is possible to check whether or not drugs are correctly packaged. However, a pharmacist needs to perform inspection while the pharmacist himself or herself determines to which master image which portion of a captured image corresponds. Therefore, since high focus is required by the pharmacist, the work load is high.

In order to solve the aforementioned problem, it is an object of the present invention to provide a drug inspection support apparatus and method capable of realizing efficient visual inspection work performed by a pharmacist upon inspection of drugs.

In order to achieve the aforementioned object, the present invention provides a drug inspection support apparatus for inspecting drugs, which are prepared based on prescription information and are packaged in a prescription bag, including: a first drug determination section configured to compare drug master images from a drug database, which stores drug master images of drugs that can be prepared, with a captured image obtained by capturing an image of prepared drugs and determining to which drug each drug present in the captured image corresponds; and a list creation section configured to create a list displaying drug master images of drugs prepared according to a prescription and drug area images, which are determined as respective drugs in the captured image, so that positions of the drug master images and the drug area images are aligned with one another.

In the present invention, the list creation section may display the drug area images of which sizes are enlarged or reduced so that sizes of the drug area images and the drug master images are same, in the list.

In addition, in the present invention, the list creation section may display the drug area images of which orientation are rotated so that orientations of the drug area images and the drug master images are same, in the list.

The list creation section may align the drug master images in order according to a difference between a position in feature space of each drug and a position in feature space of other drugs.

The list created by the list creation section may be displayed on a display device, and the drug area image selected by a user from the list is enlarged.

The list may further include a check box for a pharmacist.

The list creation section may store the created list in a storage device in association with the prescription information.

Either one of a row and a column of the list may correspond to the drug prepared according to the prescription, and the other one of the row and the column may correspond to the prescription bag. The drug master images of the prepared drugs may be arranged side by side in the either one of the row and the column. For each prescription bag, a drug area image of each drug included in the captured image may be arranged in the row or the column corresponding to the determined drug.

The drug inspection support apparatus of the present invention may further include an inspection result determination section configured to determine whether or not the prepared drugs and the number thereof match the prescription information based on the prescription information. In this case, the list may include a field for displaying a determination result of the inspection result determination section.

The drug inspection support apparatus of the present invention may further include a comparison target selection section configured to acquire drug master images of the prepared drugs and drugs similar to the prepared drugs from the drug database. In this case, the first drug determination section may compare the captured image with the drug master images acquired from the drug database.

The comparison target selection section may acquire drug master images of drugs included in the prescription information and drugs similar to the drugs included in the prescription information from the drug database based on the prescription information.

In addition to those described above, the comparison target selection section may acquire, based on dispensing information for specifying drugs used at the time of at the time of preparation, the drug master images of drugs included in the dispensing information and the drugs similar to the drugs included in the dispensing information from the drug database.

The captured image may be an image obtained by capturing the prescription bag in which the prepared drugs are packaged.

Drugs to be taken at each specified dosage time may be packaged in the prescription bag.

The list creation section may arrange the prescription bags having a same specified dosage time side by side in a continuous manner in the list.

The first drug determination section may extract characters from the captured image, recognize the characters, and determine drugs present in the captured image based on the recognized characters.

The drug inspection support apparatus of the present invention may further include a second drug determination section configured to perform primary drug determination by extracting an outer shape feature and a size feature of each drug from the captured image of the prepared drugs and comparing the extracted outer shape feature and the extracted size feature with an outer shape feature and a size feature of each of the prepared drugs. In this case, the first drug determination section may compare the captured image with the drug master image for each drug that cannot be determined by the second drug determination section.

The second drug determination section may extract an outer shape feature and a size feature from a captured image that is captured by emitting illumination light to the prepared drugs from an opposite side to imaging means.

The drug inspection support apparatus of the present invention may further include: a database registration section configured to prompt a user to designate a partial image of each prepared drug included in the captured image and additionally registering the designated partial image in the drug database as a drug master image when there is no drug master image of the prepared drugs in the drug database.

The drug inspection support apparatus of the present invention may further include a database registration section configured to acquire drug master images of the prepared drugs by accessing a remote master database when there is no drug master image of the prepared drugs in the drug database.

In addition, the present invention provides a drug inspection support method for inspecting drugs, which are prepared based on prescription information and are packaged in a prescription bag, using a drug inspection support apparatus including: comparing drug master images from a drug database, which stores drug master images of drugs that can be prepared, with a captured image obtained by capturing an image of prepared drugs and determining to which drug each drug present in the captured image corresponds by the drug inspection support apparatus; and creating a list displaying drug master images of drugs prepared according to a prescription and drug area images, which are determined to be respective drugs in the captured image, so that positions of the drug master images and the drug area images are aligned with one another by the drug inspection support apparatus.

In the present embodiment, by comparing a captured image obtained by capturing an image of prepared drugs with a drug master image from the drug database, it is determined which kinds of drugs the drugs included in the captured image are. Then, a list displaying drug master images of drugs, which are prepared according to a prescription, and drug area images, which are determined to be respective drugs in the captured image, so that the positions thereof are aligned with one another is created. For example, a pharmacist can easily visually check whether or not drugs are packaged in each prescription bag as prescribed, by making the column of the list correspond to the drug and displaying the drug master image and the drug area image determined as being the drug in each column. In addition, when there is an erroneous determination made by the drug determination section, an image of a different drug is included in the drug area images aligned in a column. Therefore, since it is possible to easily recognize the erroneous determination of the drug determination section, it is possible to realize efficient visual inspection work performed by the pharmacist upon inspection of drugs.

BRIEF DESCRIPTION OF THE DRAWINGS

FIG. 2 is a diagram showing an example of information stored in a drug database.

FIG. 3 is a diagram showing the relationship between prescribed drugs and a drug image acquired by a comparison target selection section.

DESCRIPTION OF THE PREFERRED EMBODIMENTS

Prior to the description of embodiments of the present invention, a schematic flow from the time of prescription of drugs by a doctor until the prepared drugs are handed to a patient will be described. After a prescription is written by a doctor, a pharmacist dispenses drugs specified in the prescription from packaging materials, such as a PTP (press through package), to a tray or the like by one bag at a time. Alternatively, prescription information may be input into an automatic drug dispenser, and the automatic drug dispenser may dispense the drugs. A packaging device packages dispensed drugs, for example, for each specified dosage time according to prescription information. The packaged drugs are passed to the patient after final checking or the like by the pharmacist. The drug inspection support apparatus of the present invention supports pharmacist inspection regarding whether or not the drugs passed to a patient are as prescribed.

Figure 1:
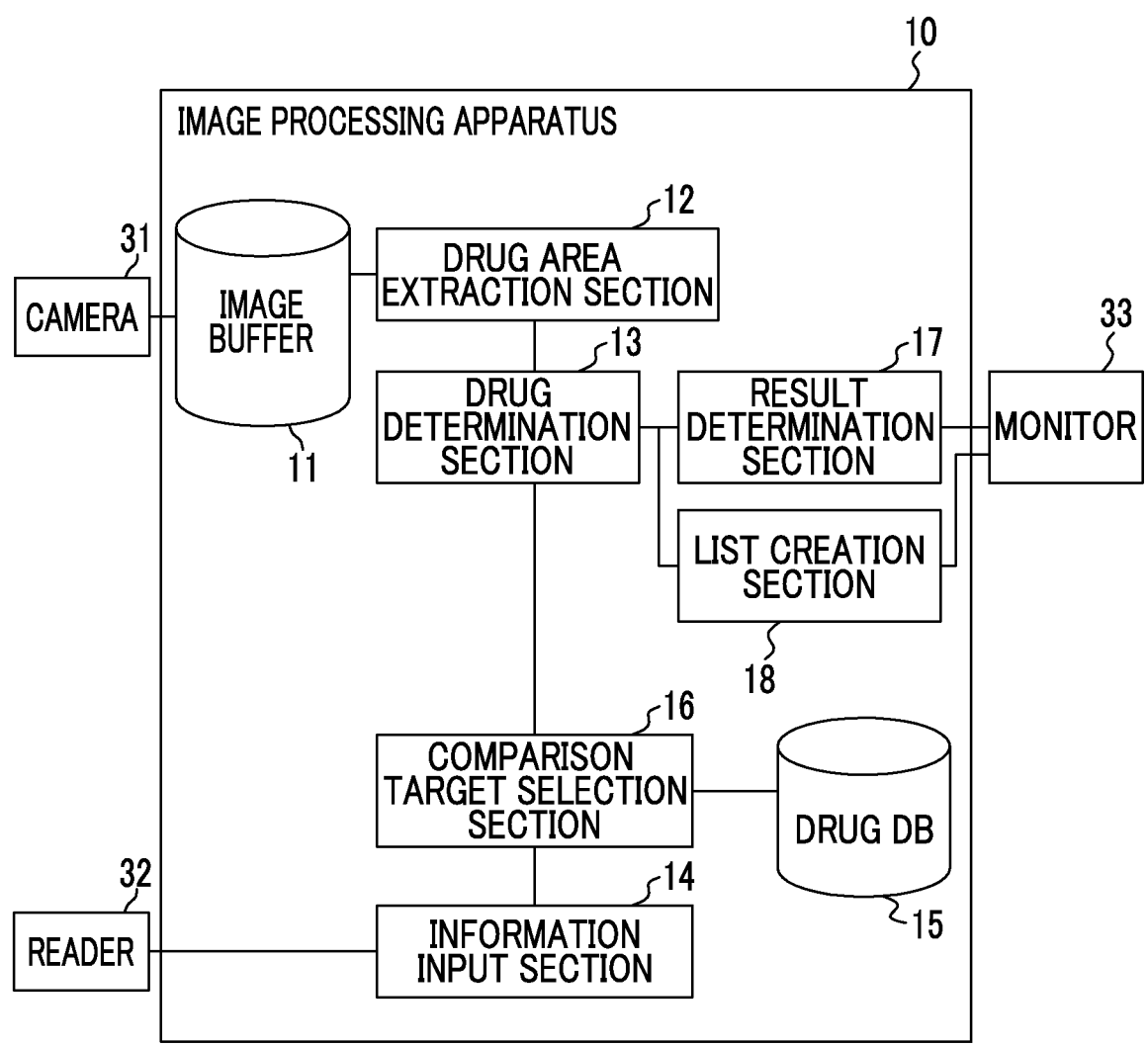
FIG. 1 is a block diagram showing the configuration of a drug inspection support system including a drug inspection support apparatus (image processing apparatus) of an embodiment of the present invention.

Hereinafter, embodiments of the present invention will be described in detail with reference to the diagrams. FIG. 1 shows the configuration of a drug inspection support inspection system including a drug inspection support apparatus (image processing apparatus) of an embodiment of the present invention. The drug inspection support system includes a drug inspection support apparatus 10, an imaging apparatus (camera) 31, a reader 32, and a monitor 33. The drug inspection support apparatus 10 includes an image buffer 11, a drug area extraction section 12, a drug determination section 13 (first drug determination section), an information input section 14, a drug database 15, a comparison target selection section 16, an inspection result determination section 17, and a list creation section 18.

In addition, the drug inspection support apparatus 10 is a computer including a central processing unit (CPU), a main memory, and a nonvolatile storage device, for example. For example, when a program stored in the storage device is loaded to the main memory and the CPU executes the loaded program, each functional block of the drug area extraction section 12, the drug determination section (first drug determination section) 13, the information input section 14, the comparison target selection section 16, the inspection result determination section 17, and the list creation section 18 functions.

The camera 31 captures an image of packaged (prepared) drugs. For example, the camera 31 captures a prescription bag in which prepared drugs are packaged. Alternatively, drugs placed on a tray before being packaged may be captured. During the capture, it is preferable to eliminate overlapping between drugs by applying vibration, for example. The image buffer 11 stores a captured image that has been captured by the camera 31. The drug area extraction section 12 reads the captured image of drugs from the image buffer 11, and extracts a drug area portion (drug area image) from the captured image. For example, when a plurality of drugs are packaged in one prescription bag, the drug area extraction section 12 extracts the drugs so as to be separated from each other.

The reader 32 reads prescription information. For example, the reader 32 reads information, such as the prescribed drugs, the number of drugs, and the specified dosage time, from the prescription written on the paper by optical character recognition (OCR). When a bar code indicating the information regarding the prescribed drugs is present in the prescription, it is possible to read the bar code to read the information, such as prescribed drugs, the number of drugs, and specified dosage time. The information input section 14 receives the prescription information read by the reader 32. Alternatively, the information input section 14 may communicate with a computer, which is used by a doctor who has written the prescription, by cable or wirelessly to receive the prescription information from the computer of the doctor. In addition, an operator may read a prescription and input the prescription information using a keyboard or the like.

In the drug database 15, various kinds of information regarding drugs that can be prepared are stored. Image information of drugs (drug master image) is included in the information stored in the drug database 15. The drug determination section 13 that serves as image checking means compares the captured image of the drug from the camera 31 with the drug master image from the drug database 15, and determines drugs present in the captured image and the number thereof. The drug determination section 13 determines to which drug each drug area corresponds by extracting a feature amount from the image and performing feature amount comparison.

The comparison target selection section 16 acquires drug master images to be checked by the drug determination section 13 from the drug database 15. For example, the comparison target selection section 16 acquires drug master images of drugs, which should be prepared according to the prescription, and drugs similar thereto from the drug database 15. More specifically, the comparison target selection section 16 acquires drug master images of drugs included in prescription information and drugs similar thereto from the drug database 15 based on the prescription information input from the information input section 14.

As drug master images of drugs similar to prescribed drugs, the comparison target selection section 16 acquires drug master images of drugs located at a distance within a predetermined threshold value from a position in the feature space of the prescribed drugs, for example. As features of drugs, a pattern feature indicating the brightness distribution on the drug surface including characters, an outer shape feature indicating a contour shape, a size feature indicating the area or the lengths of the long and short axes, a color feature, and the like can be considered. As another example, a list of drugs similar to each drug may be set in the drug database 15 for each drug, and drug master images of similar drugs may be acquired with reference to the list.

The drug determination section 13 compares the captured image of drugs from the camera 31 with the drug master image acquired from the drug database 15 by the comparison target selection section 16. For example, the drug determination section 13 determines to which drug each drug area corresponds by extracting a feature amount from the image of each drug area extracted by the drug area extraction section 12 and comparing the feature amount with the feature amount extracted from the drug master image. The drug determination section 13 determines that the drug with the closest feature amount is the drug of each drug image (captured image), for example.

Based on the prescription information, the inspection result determination section 17 determines whether or not the prepared drugs and the number thereof match the prescription information. For example, the inspection result determination section 17 determines whether or not types of drugs and the number thereof are correct for each packaging. When it is determined that the prepared drugs and the number thereof match the prescription information, the inspection result determination section 17 displays an inspection result OK on the monitor 33. Alternatively, using a printer (not shown), a display showing inspection OK may be printed on the prescription bag.

FIG. 2 shows an example of information stored in the drug database 15. The drug database 15 stores, for example, a drug ID, a drug name, a drug master image, and a similar drug list for each drug. The drug ID is an identifier for uniquely identifying a drug, and the drug name is the name of a drug. In the similar drug list, IDs of one or more drugs similar to a drug identified by the drug ID are stored. In the example shown in FIG. 2, a drug of drug name "drug A" is similar to drugs of drug names "drug X" and "drug Y". In this case, when "drug A" is included in the prescription information, the comparison target selection section 16 acquires drug master images of "drug X" and "drug Y" in addition to the drug master image of "drug A".

FIG. 3 shows the relationship between prescribed drugs and drug master images acquired by the comparison target selection section 16. For example, it is assumed that three drugs of drug A, drug B, and drug C have been prescribed in a prescription. When the information shown in FIG. 2 is stored in the drug database 15, the comparison target selection section 16 acquires drug master images of the drug A, the drug B, and the drug C and drug master images of drug X, drug Y, and drug Z similar thereto from the drug database 15. The drug determination section 13 compares the image of each drug area extracted by the drug area extraction section 12 with the drug master image acquired by the comparison target selection section 16, and determines to which of the drugs A, B, C, X, Y, and Z, which are targets to be compared, the image of each drug area extracted by the drug area extraction section 12 corresponds based on the feature amount difference.

Referring back to FIG. 1, the list creation section 18 creates a list of drugs contained in each prescription bag. The list creation section 18 creates a list displaying the drug master images of drugs, which should be prepared according to the prescription, and drug area images, which are determined to be respective drugs in the captured image, so that the positions thereof are aligned with one another. In the list, for example, a column corresponds to each drug that should be prepared according to the prescription, and a row corresponds to a prescription bag. The correspondence of rows and columns may be reversed. The list creation section 18 arranges the drug master images of the drugs to be prepared side by side in each column. For example, when there are ten kinds of drugs to be prepared, ten drug master images are arranged in columns corresponding to the respective drugs. In addition, for each prescription bag, the list creation section 18 arranges the drug area image of each drug included in the captured image in the column corresponding to the drug determined by the drug determination section 13.

The list creation section 18 displays the created list on the monitor 33. When a user selects a drug area image on the displayed list, the list creation section 18 may display the selected drug area image in an enlarged manner. Instead of displaying the created list on the monitor 33 or in addition to displaying the created list on the monitor 33, the list may be printed on paper.

Figure 4:
FIG. 4 is a diagram showing an example of a created list.
Figure 4:
Figure 4:
Figure 4:
Figure 4:
Figure 4:
Figure 4:
Figure 4:
Figure 4:
Figure 4:
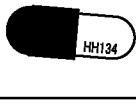
Figure 4:

FIG. 4 shows an example of the created list. In FIG. 4, a column corresponds to each drug, and a row corresponds to each prescription bag. For example, it is assumed that five kinds of drugs of drug 1 to drug 5 are prescribed in a prescription. In addition, it is assumed that 10-days of drugs are prescribed and the specified dosage time is three times of, morning, daytime, and evening. In this case, prescribed drugs are packaged in prescription bags of 3×10=30 bags, and there are 30 prescription bags to be inspected. The camera 31 captures the image of each of the 30 prescription bags, and the drug determination section 13 determines which drugs the drugs present in each prescription bag are.

The name or the like of each drug corresponding to each column is arranged at the top of the list, and the drug master image of each drug is arranged at the next stage. For example, for each of the 30 prescription bags, the list creation section 18 arranges the drug area image, which is determined to be the drug, in the column of the corresponding drug according to the determination result in the drug determination section 13. For example, the drug area image that is determined to be the drug 1 is arranged in the column of the drug 1, and the drug area image that is determined to be the drug 2 is arranged in the column of the drug 2. A pharmacist can easily check whether or not drugs are packaged in each prescription bag as prescribed by comparing the images of the column corresponding to each of the drugs.

It is preferable that the list creation section 18 arrange drug area images, which are enlarged or reduced, so that the sizes of the drug master images and the drug area images arranged in the list are the same, in the list. In addition, it is preferable that the list creation section 18 arrange drug area images, which are rotated, so that the orientation (angle) of each drug master image and the orientation of each drug area image arranged in the list are the same, in the list. The orientation of each drug in the captured image may be determined from the character recognition result of characters given to the drug. Alternatively, for a drug with multiple colors, such as a capsule, the orientation of the drug may be determined from the pattern of the arrangement of the color. Visual inspection becomes easier by making the size or the orientation equal in the list.

When creating a list, the list creation section 18 may align drugs by sorting the drugs according to the similarity between drugs. For example, drugs (drug master images) may be aligned in order according to a difference between the position in the feature space of each drug when extracting the feature amount from the drug master image of each drug and the position in the feature space of other drugs. For example, a drug having low similarity with other drugs (having a large feature amount difference) may be arranged on the left side toward the sheet surface of FIG. 4, and a drug having high similarity with other drugs (having a small feature amount difference) may be arranged on the right side. In this case, the drugs on the left side of the sheet surface of FIG. 4 are drugs that can be determined at a glance, while similar drugs appear rightward and these drugs become drugs that need to be observed carefully.

In FIG. 4, images of drugs contained in corresponding prescription bags in order of the morning, daytime, and evening of the first day and the morning, daytime, and evening of the second day are aligned from the top of the paper. However, drugs to be taken may change with the specified dosage time. In this case, sorting the drugs in units of specified dosage time may be convenient in view of checking. The list creation section 18 may arrange prescription bags having the same specified dosage time in the list side by side. Specifically, it is possible to create a list in which the prescription bags corresponding to the specified dosage time "morning" of the first to tenth days are continuously arranged, the prescription bags corresponding to the specified dosage time "daytime" of the first to tenth days are continuously arranged next, and the prescription bags corresponding to the specified dosage time "evening" of the first to tenth days are continuously arranged next by performing sorting based on the specified dosage time.

The arrangement of drugs and prescription bags in the list may be arbitrarily changed by the user. For example, the user can arbitrarily designate the column to which each drug corresponds. In addition, a display switching button may be provided so that criteria for sorting rows or columns can be arbitrarily changed. For example, by pressing the switching button, the user can display rows by sorting the rows in order of dosage date and time or can display rows by sorting the rows in units of specified dosage time.

Although not shown in FIG. 4, the list may include a check box for a pharmacist. In addition, the list may include a field for displaying an inspection result of the inspection result determination section 17. The user (pharmacist) can check whether or not packaged drugs are the same as the prescription by comparing the drug area image listed for each prescription bag with the drug master image. In particular, it is preferable to inspect carefully a prescription bag determined as NG by the inspection result determination section 17. After confirming that the packaged drugs are the same as the prescription by visual inspection, a check is put in the list. It is preferable to proceed to pass the drugs to the patient after all checks are completed.

Figure 5:
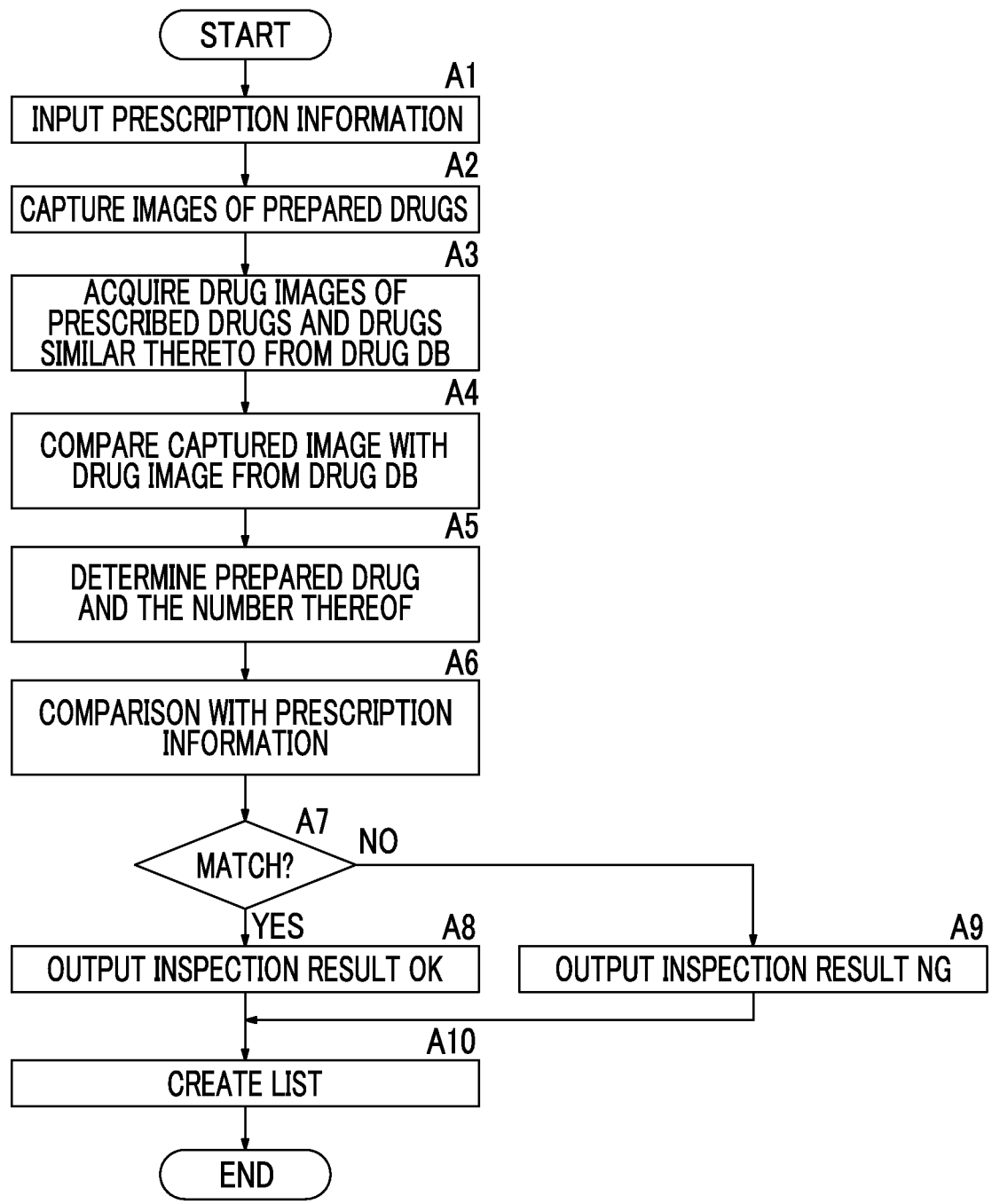
FIG. 5 is a flowchart showing the operation procedure of the drug inspection support system of a first embodiment.

FIG. 5 shows the operation procedure in the drug inspection support system of the first embodiment. The information input section 14 receives prescription information from the reader 32 (step A1). The camera 31 captures the image of the drugs packaged by a packaging device or the like or the drugs in a state where drugs to be packaged are placed on a tray corresponding to each prescription bag or the like (step A2). The captured image is stored in the image buffer 11. The comparison target selection section 16 acquires drug master images of prescribed drugs and drugs similar thereto based on the prescription information input in step A1 (step A3). The checking range is expanded to a similar range by acquiring not only the images of prescribed drugs but also the images of drugs similar thereto.

The drug area extraction section 12 extracts a drug area image from the captured image that has been captured by the camera 31. The drug determination section 13 compares each of the extracted drug area images with each of the drug master images acquired by the comparison target selection section 16 (step A4). The drug determination section 13 determines the packaged drugs and the number thereof by comparing the feature amount extracted from the drug area with the feature amount extracted from the drug master image acquired by the comparison target selection section 16 (step A5). For example, for each specified dosage time, the drug determination section 13 determines to which drug the drug packaged in a prescription bag corresponding to each specified dosage time corresponds and how many packets of the drug are present.

In addition, when a plurality of drug master images having a feature amount close to the feature amount extracted from the drug area image are present as a result of comparison between the feature amount extracted from the drug area image and the feature amount extracted from the drug master image acquired by the comparison target selection section 16, the drug determination section 13 may determine that it is not possible to determine to which drug the target drug corresponds. For example, the drug determination section 13 calculates a feature amount difference between each drug master image acquired by the comparison target selection section 16 and the drug area image, and specifies a drug master image having the smallest feature amount difference (drug master image most similar to the drug area image) and a drug master image having the second smallest feature amount (drug master image second most similar to the drug area image). The feature amount difference between the drug master image most similar to the drug area image and the drug area image may be compared with the feature amount difference between the drug master image second most similar to the drug area image and the drug area image, and it may be determined that it is not possible to determine to which drug the drug of the drug area corresponds if both the differences are appropriately the same (for example, if the ratio of the feature amount differences is within a predetermined range or if the difference between the feature amount differences is within a predetermined range).

The inspection result determination section 17 compares the drugs and the number thereof determined in step A7 with the prescription information (step A6), and determines whether or not the drugs and the number thereof determined in step A7 match the prescription information (step A7). The inspection result determination section 17 determines whether or not packaged drugs match the prescription information, for example, for each prescription bag. When the packaged drugs match the prescription information, the inspection result determination section 17 outputs an inspection result of OK to the monitor 33 (step A8). When the packaged drugs do not match the prescription information, the inspection result determination section 17 outputs an inspection result of NG to the monitor 33 (step A9). When displaying the inspection result, an image captured by the camera 31 may be displayed on the monitor 33. In step A5, when it is determined that drugs cannot be determined as a result of the image checking done by the drug determination section 13, the inspection result determination section 17 may determine "indistinguishable" and display the result on the monitor 23.

When the inspection result determination section 17 determines that packaged drugs and the number thereof match the prescription information, printing for indicating that the inspection result is OK may be performed on a prescription bag corresponding to the drugs determined to match the prescription information. For example, after inspection by the drug inspection support apparatus 10, information indicating the specified dosage time, such as morning, daytime, evening, or bedtime, or the names of drugs contained in a prescription bag and the number thereof may be printed on a prescription bag determined to have an inspection result OK. Printing is preferably performed on a seal portion of the prescription bag, for example. A prescription bag determined to have an inspection result NG is preferably cut from the line of prescription bags that are continuously located so that the inspection result OK and the inspection result NG are separated from each other.

When the drug inspection support apparatus 10 determines the inspection result NG a printing apparatus may perform printing for indicating the inspection result NG or indistinguishable using the ink invisible to the human eye under visible light, such as UV ink, for example. The pharmacist can see which prescription bag has an inspection result NG by using UV light or the like. The inspection result determination section 17 may prompt the pharmacist to check an image, which is obtained by capturing a prescription bag determined to have an inspection result NG, by displaying the image on the monitor 33 in an enlarged manner. The pharmacist re-inspects visually the prescription bag determined to have an inspection result NG and inputs an inspection result OK if it is confirmed that there is no error. In this case, a printing apparatus prints information indicating the specified dosage time, such as morning, daytime, evening, or bedtime, or the names of drugs contained in a prescription bag and the number thereof. Since the characters printed with UV ink are not visible to patients, it is not necessary to eliminate the print indicating that the inspection result is NG even if the inspection result OK is obtained by re-inspection.

The list creation section 18 creates a list including the drug master images of the prescribed drugs and the drug area image determined for each prescription bag (step A10). A pharmacist checks whether or not drugs are packaged in each prescription bag as prescribed by referring to the list display of the determination result of the prepared drugs. The packaged drugs are passed to the patient after confirming that the drugs are correctly packaged. The list creation section 18 may store the created list in a storage device (not shown) so as to correspond to the prescription information.

In this case, this can be used later by searching the list using a date, a drug name, or the like.

In the present embodiment, the list creation section 18 creates a list displaying drug master images of drugs, which should be prepared according to a prescription, and drug area images, which are determined to be respective drugs in the captured image, so that the positions thereof are aligned with one another. For example, a pharmacist can easily visually check whether or not drugs are packaged in each prescription bag as prescribed by making the column of the list correspond to the drug and displaying the drug master image and the drug area image determined to be the drug in each column. In addition, when there is an erroneous determination by the drug determination section 13, an image of a different drug is included in the drug area images aligned in a column. Therefore, it is possible to easily recognize the erroneous determination of the drug determination section 13.

In the present embodiment, the comparison target selection section 16 acquires drug master images of prescribed drugs and drug master images of drugs similar to the prescribed drugs, as images to be compared, from the drug database 15. The drug determination section 13 compares the captured image of drugs, which has been captured by the camera 31, with the drug master image acquired from the drug database 15 by the comparison target selection section 16, and determines the drugs and the number thereof. By expanding the image checking target to the range including not only drugs to be prepared according to the prescription but also drugs similar thereto, it is possible to reduce the possibility of an erroneous determination indicating that the inspection result is OK even when similar drugs are prepared by mistake. In addition, since a similar range is set as an inspection target, it is possible to shorten the time required for image checking, compared with a case where image checking of all drugs registered in the drug database 15 is performed. Therefore, it is possible to increase the processing speed.

In addition, the drug inspection support apparatus 10 may be configured so that, when a drug that is not registered in the drug database 15 is prescribed, the drug area image of the drug can be registered in the drug database 15. In addition, the drug database 15 does not necessarily need to be provided in the drug inspection support apparatus 10, a drug database provided remotely may be used instead of the drug database 15 provided in the drug inspection support apparatus 10 or in addition to the drug database 15 provided in the drug inspection support apparatus 10.

Figure 6:
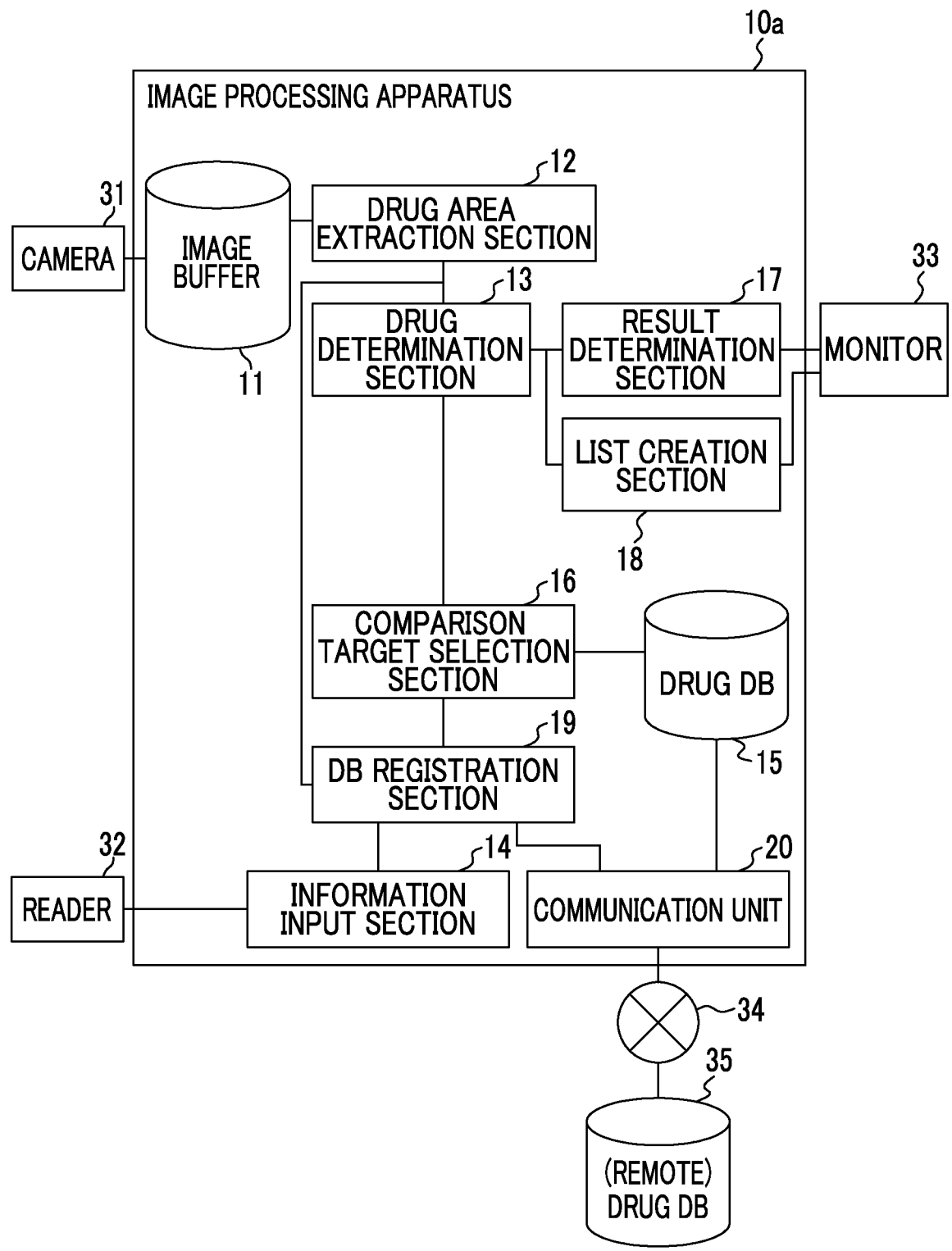
FIG. 6 is a block diagram showing a drug inspection support apparatus of a modification example.

FIG. 6 shows a drug inspection support apparatus of a modification example. A drug inspection support apparatus 10a further includes database registration section 19 and a communication unit 20. The database registration section 19 prompts a user to designate a partial image (drug area image) of a drug unregistered in the database, which is included in the captured image, when there is no information (drug master images) of prescribed drugs in the drug database 15. The user selects and designates a drug unregistered in the database from each drug area image displayed on the monitor 33, for example. The database registration section 19 additionally registers the designated drug area image in the drug database 15, as a drug master image of the drug, together with various kinds of information.

The communication unit 20 communicates with a remote drug database 35 through a network 34. The same information as in the (local) drug database 15 provided in the drug inspection support apparatus 10 is registered in the drug database 35. For example, information on new drugs or information on drugs with a low frequency of use may not be present in the drug database 15 in the drug inspection support apparatus 10, and may be present only in the remote drug database 35. When information regarding the prescribed drugs is not present in the local drug database 15, the comparison target selection section 16 accesses the remote drug database 35 through the communication unit 20 to acquire the drug master image from the remote drug database 15. The drug master image acquired at this time may be registered in the drug database 15 by the database registration section 19.

Figure 7:
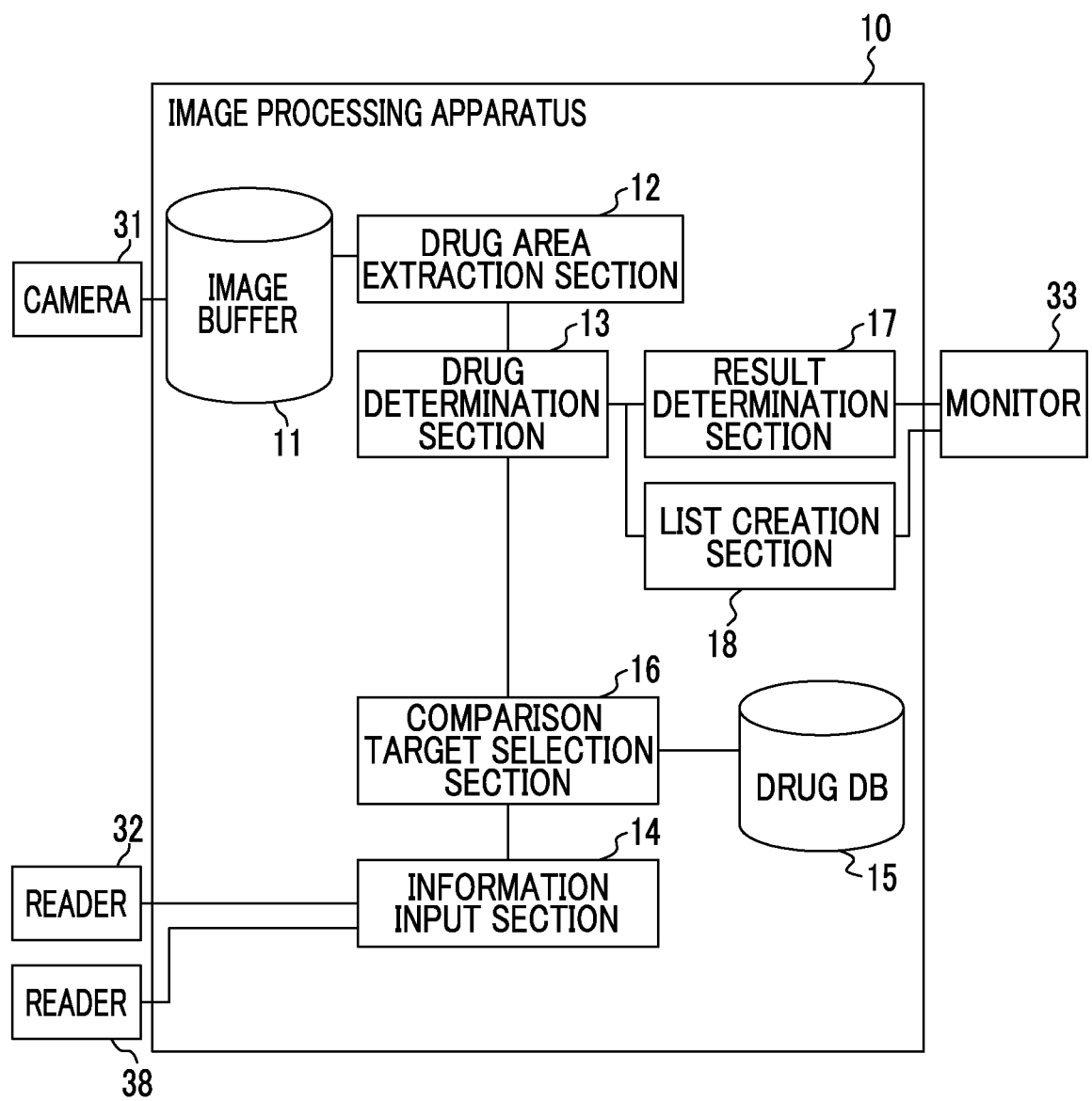
FIG. 7 is a block diagram showing a drug inspection support system including a drug inspection support apparatus of a second embodiment of the present invention.

Next, a second embodiment of the present invention will be described. FIG. 7 shows a drug inspection support system including a drug inspection support apparatus of the second embodiment of the present invention. The drug inspection support system in the present embodiment includes a reader 38 that reads dispensing information for specifying drugs used at the time of packaging (preparation) in addition to the configuration of the drug inspection support system of the first embodiment shown in FIG. 1. In the present embodiment, when acquiring the drug master images of drugs to be packaged and drugs similar thereto, the dispensing information input from the reader 38 is used. The other points may be the same as those in the first embodiment.

The reader 38 acquires information for identifying the drugs dispensed according to prescription information, for example, from an automatic drug dispenser. Alternatively, it is possible to provide an RFID tag in a tray to dispense drugs, store information for identifying the dispensed drugs in the RFID tag when dispensing drugs, and read the dispensing information from the RFID tag. The information input section 14 receives the dispensing information read by the reader 38. Alternatively, the dispensing information may be directly received from the automatic drug dispenser by cable or wireless communication with the automatic drug dispenser. The comparison target selection section 16 acquires the drug master images of drugs included in the prescription information and drugs similar thereto from the drug database 15.

In the packaging of drugs, dispensed drugs are packaged in a prescription bag. Accordingly, if there is no mistake in dispensing, dispensed drugs should be able to be correctly packaged basically as prescribed. However, it cannot be said that there is no probability of a mistake. In the present embodiment, by performing inspection in a checking range that is expanded to include drugs similar to dispensed drugs, it is possible to correctly check whether or not drugs are packaged as prescribed. Therefore, it is possible to prevent mistakes that may occur during the period from dispensing to packaging. The other effects are the same as in the first embodiment.

Figure 8:
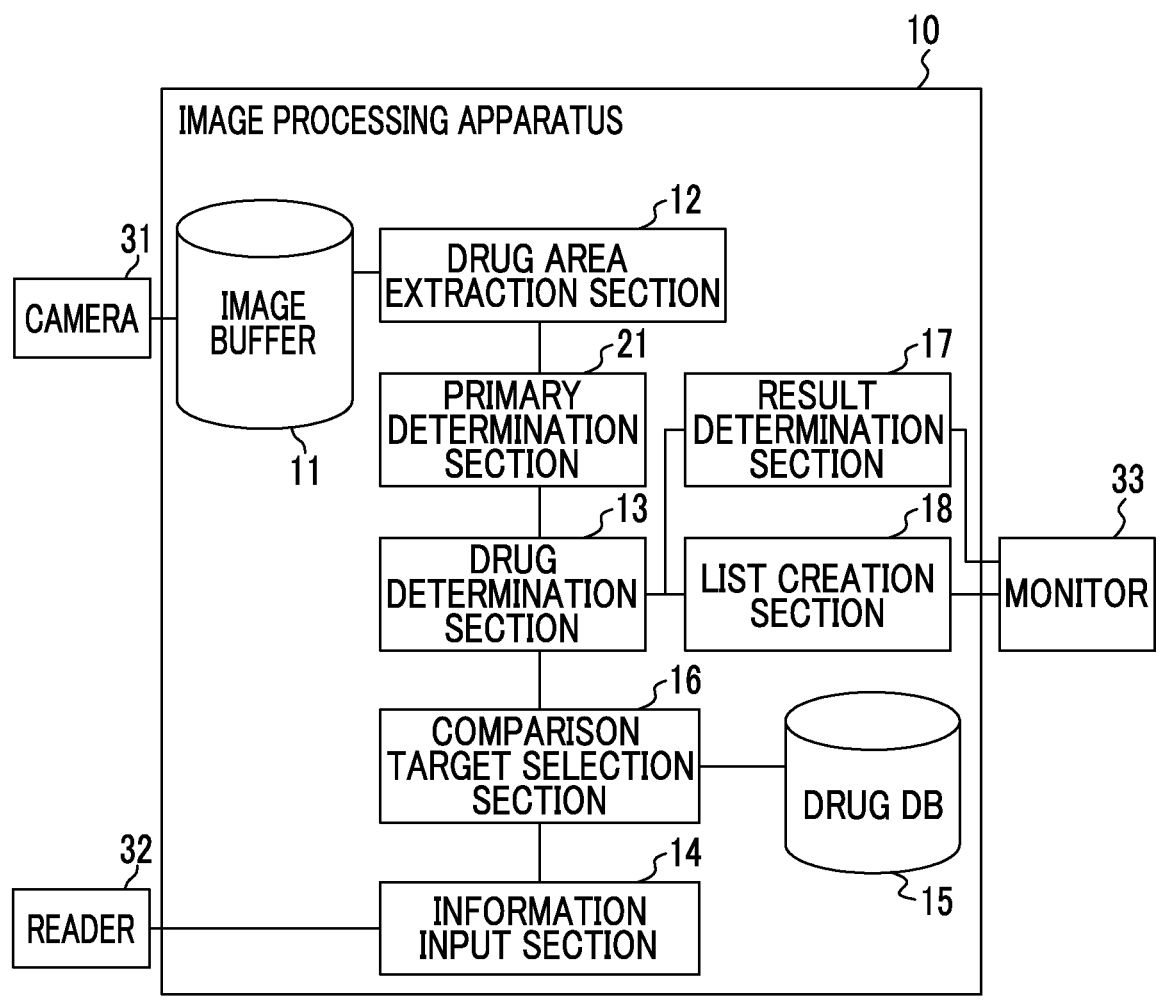
FIG. 8 is a block diagram showing a drug inspection support system including a drug inspection support apparatus of a third embodiment of the present invention.

Next, a third embodiment of the present invention will be described. FIG. 8 shows a drug inspection support system including a drug determination apparatus of the third embodiment of the present invention. A drug inspection support apparatus 10b of the present embodiment includes a primary determination section (second drug determination section) 21 in addition to the configuration of the drug inspection support apparatus 10 of the first embodiment shown in FIG. 1.

The primary determination section 21 performs primary determination of drugs by extracting the outer shape feature and the size feature of each drug from the captured image of prepared drugs and comparing the extracted outer shape feature and size feature with the outer shape feature and the size feature of each drug to be prepared. For example, the primary determination is performed for drugs that can be determined based on the outer shape feature and the size feature. For example, the primary determination section 21 checks whether or not two or more drugs having similar outer shape features and size features are included in the prescription information. When drugs having similar outer shape features and size features are included, the primary determination section 21 determines that the two or more similar drugs cannot be determined by the primary determination, and excludes the drugs from the primary determination targets. It is also possible to perform the primary determination using a color feature in addition to the outer shape feature and the size feature. The drug determination section 13 compares captured images with drug master images acquired from the drug database 15 in detail for the drugs that cannot be determined by the primary determination section 21.

Figure 9:
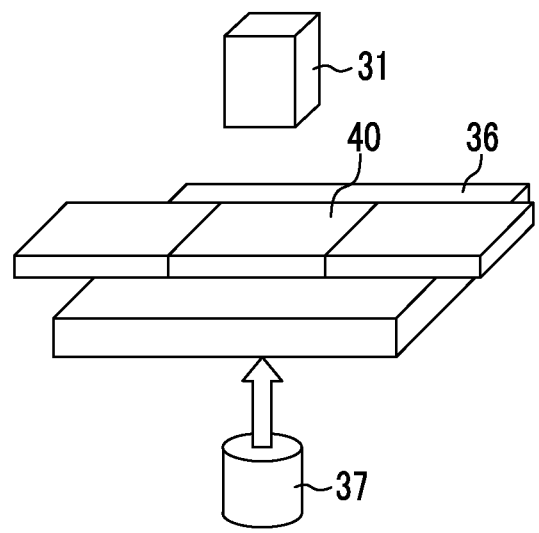
FIG. 9 is a diagram showing the image capturing of a prescription bag by a camera.

The captured images used in the drug determination section 13 and the primary determination section 21 may be different. FIG. 9 shows the image capturing of a prescription bag by the camera 31. For example, a prescription bag 40 is transported onto an inspection table 36, and drugs contained in the prescription bag 40 are captured by the camera 31. In FIG. 9, a light 37 is provided at a position facing the camera 31 with the inspection table 36 having optical transparency interposed therebetween. The camera 31 performs an image capturing in two states of a state where the light 37 is turned on and a state where the light is turned off (state where light from the camera 31 side is emitted to the prescription bag 40). By turning on the light 37 to perform an image capturing, the silhouette of drugs appears in the captured image. Accordingly, the outer shape and size of drugs become clearer.

The drug area extraction section 12 extracts a drug area from the captured image (transmitted illumination captured image) captured where the light 37 is turned on, and transmits the extracted drug area to the primary determination section 21. In addition to drug master images, the outer shape feature and the size feature of each drug are stored in the drug database 15. Accordingly, the primary determination section 21 acquires the outer shape features and the size features of drugs included in the prescription information from the drug database 15. The primary determination section 21 performs the primary determination of drugs and the number thereof by extracting the outer shape feature and the size feature of each drug from the transmitted illumination captured image and comparing these features with the outer shape feature and the size feature acquired from the drug database 15.

In addition, the drug area extraction section 12 extracts a drug area from a normal captured image captured where the light 37 is turned off and transmits the extracted drug area to the drug determination section 13. The comparison target selection section 16 acquires drugs that have not been determined by the primary determination section 21, among the drugs included in the prescription information, and drug master images of drugs similar thereto. The drug determination section 13 determines which drugs have not been determined in the primary determination and the number thereof by comparing the image of each drug area with the drug image acquired by the comparison target selection section 16. In addition, as in the second embodiment, the comparison target selection section 16 may use dispensing information instead of prescription information.

Figure 10:
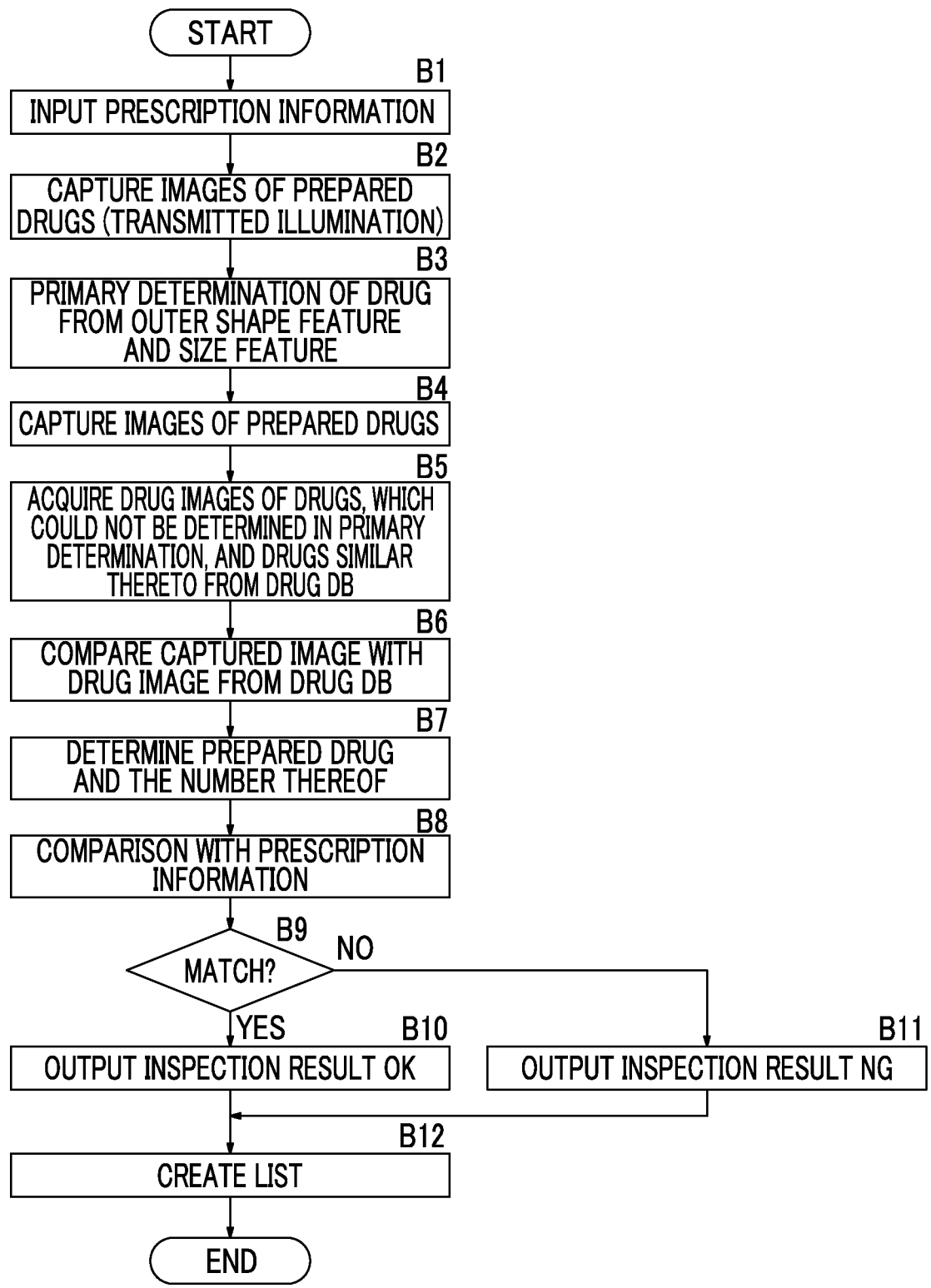
FIG. 10 is a flowchart showing the operation procedure in the drug inspection support system of the third embodiment.

FIG. 10 shows the operation procedure in the drug inspection support system of the third embodiment. The information input section 14 receives prescription information from the reader 32 (step B1). The camera 31 captures drugs packaged by a packaging device or the like or drugs in a state where drugs to be packaged are placed on a tray corresponding to each prescription bag or the like (step B2). In step B2, the camera 31 may capture the silhouette of drugs by emitting light to the drugs from the opposite side. The drug area extraction section 12 extracts a drug area from the captured image (transmitted illumination captured image) captured in step B2.

The primary determination section 21 specifies drugs that can be determined from the outer shape features and the size features with reference to the prescription information. For example, when only one drug of a plurality of packaged drugs has a long outer shape in one direction, such as a capsule, it is easy to determine a capsule-shaped drug among the plurality of packaged drugs. On the other hand, when a plurality of drugs that have shapes, such as flat round tablets, and have similar sizes are included in the plurality of packaged drugs, it is difficult to correctly determine these drugs from the outer shape features and the size features. The primary determination section 21 sets drugs for which drugs having similar outer shape features and size features are not present, among the drugs included in the prescription information, as primary determination targets, and determines the other drugs as drugs that cannot be determined in primary determination (that are excluded from the determination range).

The primary determination section 21 acquires the outer shape features and the size features of drugs, which are primary determination targets, from the drug database 15. The primary determination section 21 extracts the outer shape feature and the size feature from each drug area extracted from the drug area extraction section 12, and compares these features with the outer shape feature and the size feature acquired from the drug database 15. The primary determination section 21 determines that the drug having the smallest feature amount difference is a drug of each drug area (step B3). In this case, when a plurality of drugs having approximately the same feature amount differences are present, "indistinguishable" may be determined. For specific drugs set as the primary determination targets, the primary determination section 21 determines how many specific drugs have been packaged.

After the primary determination, detailed second determination based on image checking is performed for the drugs that could not be determined in the primary determination. The camera 31 captures drugs packaged by a packaging device or the like or drugs in a state where drugs to be packaged are placed on a tray corresponding to each prescription bag or the like (step B4). In this case, no light is emitted from the opposite side to the camera 31, and the color of a drug or the character, pattern, or the like attached to the drug can be visually recognized in the captured image. In addition, when the transmitted illumination captured image is not used in the primary determination, step B4 may be omitted, and the primary determination and the second determination may be performed using the same captured image. The comparison target selection section 16 acquires drug master images of drugs that have not been determined in the primary determination, among the prescribed drugs, and drug master images of drugs similar thereto (step B5). Since some drugs are determined in the primary determination, it is possible to reduce the number of drugs for which detailed image checking is performed.

The drug area extraction section 12 extracts a drug area from the captured image captured in step B4. The drug determination section 13 compares each of the extracted drug areas excluding the drug areas determined in the primary determination with each of the drug master images acquired by the comparison target selection section 16 (step B6). The drug determination section 13 determines drugs, which have not been determined in the primary determination, and the number thereof by comparing the feature amount extracted from the drug area with the feature amount extracted from the drug master image acquired by the comparison target selection section 16 (step B7). In addition, when all drugs can be determined in the primary determination, steps B4 to B7 can be omitted.

The inspection result determination section 17 compares the drugs and the number thereof determined in steps B3 and B7 with the prescription information (step B8), and determines whether or not the drugs and the number thereof determined in steps B3 and B8 match the prescription information (step B9). The inspection result determination section 17 determines whether or not packaged drugs match the prescription information, for example, for each prescription bag. When the packaged drugs match the prescription information, the inspection result determination section 17 outputs an inspection result of OK to the monitor 33 (step B10). When the packaged drugs do not match the prescription information, the inspection result determination section 17 outputs an inspection result of NG to the monitor 33 (step B11). When displaying the inspection result, at least one of the images captured in steps B2 and B4 may be displayed on the monitor 33.

The list creation section 18 creates a list including the drug master images of the prescribed drugs and the drug area image determined for each prescription bag (step B12). As the drug area image displayed in the list at this time, it is possible to use the image of the drug area extracted from the captured image captured in step B4. The pharmacist checks whether or not drugs are packaged in each prescription bag as prescribed by referring to the list display of the determination result of the prepared drugs. The packaged drugs are passed to the patient after confirming that the drugs are correctly packaged. The list creation section 18 may store the created list in a storage device (not shown) so as to correspond to the prescription information, similar to the first embodiment.

In the present embodiment, drugs that can be determined from the outer shape features and the size features are determined by the primary determination section 21, and image checking for drugs that cannot be determined by the primary determination section 21 (drugs that are not determination targets) is performed by the drug determination section 13. Determination of drugs based on the outer shape features and the size features can be performed more easily than determination based on image checking. In the present embodiment, since the number of drugs that are image checking targets can be reduced using the primary determination section 21, it is possible to perform drug determination more efficiently by reducing the number of image checking targets. The other effects are the same as those of the first and second embodiments.

In addition, a case can be considered in which, if a certain drug and another drug are too similar, both drugs cannot be clearly distinguished by image checking with the drug determination section 13. When drugs that have too similar features and cannot be determined by image analysis are prescribed at the same time, the drugs may be excluded from targets of image analysis. For example, a list of drugs that cannot be determined by image analysis due to high degrees of similarity (simultaneously indistinguishable drug list) is stored in the drug database 15. Then, when drugs included in the simultaneously indistinguishable drug list are prescribed at the same time, the simultaneously indistinguishable drugs prescribed at the same time are stored in a determination exclusion list, and these drugs may be excluded from targets to be checked by the drug determination section 13. For drugs excluded from drug determination targets, drug master images and drug area images extracted from the captured image may be displayed together on the rightmost side of the list, for example.

In each of the embodiments described above, the drug determination section 13 sets drug master images of prescribed or dispensed drugs and drug master images of drugs similar to the prescribed or dispensed drugs, which have been acquired by the comparison target selection section 16, as image checking targets. However, the present invention is not limited to this. For example, the drug determination section 13 may compare the drug master images of drugs included in the prescription information or dispensing information with each drug area image in the captured image. In addition, the drug determination section 13 may compare each drug master image registered in the drug database 15 with each drug area image in the captured image, without narrowing the checking range specifically.

In each of the embodiments described above, the drug determination section 13 may include character recognition means for extracting characters from an image and recognizing the characters. For example, it is also possible to extract a drug name or a character string unique to a drug from a captured image, recognize the drug name or the character string, and determine drugs present in the captured image based on the recognized character. In addition, although one camera is shown in FIG. 9, two cameras may be provided in the third embodiment so that a captured image in a state where the light 37 is turned on and a captured image in a state where the light 37 is turned off are captured by separate cameras.

In each of the embodiments described above, the drug determination section 13 determines to which drug the drug area image (captured image) corresponds and determines the number of drugs. However, it is possible to omit the determination of the number of drugs. For example, when two of the same drugs are packaged, it is preferable to perform drug determination (image checking) after excluding a drug which has been successfully checked first from the checking target. Even if the number of drugs is not determined, a list of packaged drugs can be created by extracting the drug area from the captured image, comparing the drug area with the drug master image group of drugs to be packaged, and arranging them so as to be aligned in order of similarity.

While the present invention has been described based on the preferred embodiments, the drug inspection support apparatus and method of the present invention is not limited only to the embodiments described above, and various modifications and changes from the configuration of the embodiments described above are also included in the range of the present invention.

What is claimed is:

1. A drug inspection support apparatus for inspecting drugs that are prepared based on prescription information and are packaged in a prescription bag, comprising:
a storage device including a drug database, and
a processor, the processor being configured to:
perform primary drug determination by
extracting an outer shape feature and a size feature of each drug from the captured image of the prepared drugs, comparing the extracted outer shape feature and the extracted size feature with an outer shape feature and a size feature of each of the drugs from the drug database, and determining that a drug from the captured image of the prepared drugs corresponds to a drug from the drug database when the drugs have a smallest feature amount difference therebetween; and the processor being further configured to, for each drug that cannot be determined by the primary drug determination:

compare drug master images from the drug database, which stores drug master images of drugs that can be prepared, with a captured image obtained by capturing the prescription bag in which the prepared drugs are packaged; and determine which kind of drug each drug present in the captured image corresponds to based on a feature amount difference; and create a list displaying the drug master images of the drugs that are prepared according to a prescription and drug area images, wherein the drug area images are the respective drugs in the captured image, so that positions of the drug master images and the drug area images are aligned with one another; and wherein when columns of the list correspond to the drug master images of the drugs that are prepared according to the prescription and are arranged side by side in the columns, rows of the list correspond to the prescription bag and a drug area image of the prescription bag is arranged in a row at a column corresponding to the drug master image of the drug, or when rows of the list correspond to the drug master images of the drugs that are prepared according to the prescription and are arranged side by side in the rows, columns of the list correspond to the prescription bag and a drug area image of the prescription bag is arranged in a column at a row corresponding to the drug master image of the drug.

2. The drug inspection support apparatus according to claim 1, wherein the processor further configured to display the drug area images of which sizes are enlarged or reduced so that sizes of the drug area images and the drug master images are same, in the list.

3. The drug inspection support apparatus according to claim 1, wherein the processor further configured to display drug area images of which orientations are rotated so that orientations of the drug area images and the drug master images are same, in the list.

4. The drug inspection support apparatus according to claim 1, wherein the processor further configured to align the drug master images in order according to a difference between a position in feature space of each drug and a position in the feature space of other drugs.

5. The drug inspection support apparatus according to claim 1, wherein the list is displayed on a display device, and the drug area image selected by a user on the list is enlarged.

6. The drug inspection support apparatus according to claim 1, wherein the list further includes a check box for a pharmacist.

7. The drug inspection support apparatus according to claim 1, wherein the processor further configured to store the created list in a storage device in association with the prescription information.

8. The drug inspection support apparatus according to claim 1, the processor further configured to determine whether or not the prepared drugs and the number the prepared drugs match the prescription information based on the prescription information, wherein the list includes a field for displaying a result of said determination.

9. The drug inspection support apparatus according to claim 1, the processor further configured to:

acquire drug master images of the drugs that are prepared according to the prescription from the drug database, and compare the captured image with the drug master images acquired from the drug database.

10. The drug inspection support apparatus according to claim 9, wherein the processor further configured to acquire drug master images of drugs included in the prescription information and drugs similar to the drugs included in the prescription information from the drug database based on the prescription information.

11. The drug inspection support apparatus according to claim 9, wherein the processor further configured to acquire, based on dispensing information for specifying drugs used at the time of preparation, the drug master images of drugs included in the dispensing information and the drugs similar to the drugs included in the dispensing information from the drug database.

12. The drug inspection support apparatus according to claim 1, wherein drugs to be taken at each specified dosage time are packaged in the prescription bag.

13. The drug inspection support apparatus according to claim 12, wherein the processor further configured to arrange the prescription bags having a same specified dosage time side by side in a continuous manner in the list.

14. The drug inspection support apparatus according to claim 1, wherein the processor further configured to extract characters from the captured image, recognizes the characters, and determines drugs present in the captured image based on the recognized characters.

15. The drug inspection support apparatus according to claim 1, wherein the processor further configured to extract an outer shape feature and a size feature from a captured image that is captured by emitting illumination light to the prepared drugs from an opposite side to imaging means.

16. The drug inspection support apparatus according to claim 1, the processor further configured to prompt a user to designate a partial image of each prepared drug included in the captured image and registering the designated partial image in the drug database as a drug master image when there is no drug master image of the drugs that are prepared according to the prescription in the drug database.

17. The drug inspection support apparatus according to claim 1,
the processor further configured to acquire drug master images of the drugs that are prepared according to the prescription by accessing a remote master database when there is no drug master image of the drugs that are prepared according to the prescription in the drug database.

18. A drug inspection support method for inspecting drugs that are prepared based on prescription information and are packaged in a prescription bag using a drug inspection support apparatus, the method comprising:
performing primary drug determination by
extracting an outer shape feature and a size feature of each drug from the captured image of the prepared drugs,
comparing the extracted outer shape feature and the extracted size feature with an outer shape feature and a size feature of each of the drugs from the drug database, and
determining that a drug from the captured image of the prepared drugs corresponds to a drug from the drug database when the drugs have a smallest feature amount difference therebetween; and for each drug that cannot be determined by the primary drug determination,
comparing the drug master images from a drug database, which stores drug master images of drugs that can be prepared, with a captured image obtained by capturing the prescription bag in which the prepared drugs are packaged,
determining which drug each drug present in the captured image corresponds to based on a feature amount difference; and
creating a list displaying drug master images of drugs that are prepared according to a prescription and drug area images, wherein the drug area images are the respective drugs in the captured image, so that positions of the drug master images and the drug area images are aligned with one another, and
wherein when columns of the list correspond to the drug master images of the drugs that are prepared according to the prescription and are arranged side by side in the columns, rows of the list correspond to the prescription bag and a drug area image of the prescription bag is arranged in a row at a column corresponding to the drug master image of the drug, or,
when rows of the list correspond to the drug master images of the drugs that are prepared according to the prescription and are arranged side by side in the rows, columns of the list correspond to the prescription bag and a drug area image of the prescription bag is arranged in a column at a row corresponding to the drug master image of the drug.

19. The drug inspection support apparatus according to claim 1, further comprising:
a monitor for displaying the created list.

20. The drug inspection support method according to claim 18, further comprising:
displaying the created list on a monitor.

* * * * *